United States Patent
Pauly et al.

(10) Patent No.: US 6,243,608 B1
(45) Date of Patent: *Jun. 5, 2001

(54) IMPLANTABLE DEVICE WITH OPTICAL TELEMETRY

(75) Inventors: Robert L. Pauly, Friendswood; Travis H. Bendele, Devine, both of TX (US)

(73) Assignee: Intermedics Inc., Angleton, TX (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/096,877

(22) Filed: Jun. 12, 1998

(51) Int. Cl.$^7$ ..................................................... A61N 1/08
(52) U.S. Cl. .............................. 607/60; 607/32; 128/903
(58) Field of Search ....................... 607/60, 52; 128/903, 128/908

(56) References Cited

U.S. PATENT DOCUMENTS

| | | | |
|---|---|---|---|
| 3,867,950 | * 2/1975 | Fischell | 607/33 |
| 4,041,954 | 8/1977 | Ohara | 128/419 PT |
| 4,361,153 | 11/1982 | Slocum | 128/419 P |
| 5,314,453 | 5/1994 | Jeutter | 607/61 |
| 5,350,413 | 9/1994 | Miller | 607/61 |
| 5,387,259 | * 2/1995 | Davidson | 128/908 |
| 5,411,537 | 5/1995 | Munshi | 607/33 |
| 5,556,421 | 9/1996 | Prutchi | 607/36 |
| 5,617,235 | 4/1997 | Abrahamson | 359/142 |
| 5,626,619 | 5/1997 | Jacobsen | 607/5 |
| 5,690,690 | 11/1997 | Nappholz | 607/30 |
| 5,730,125 | * 3/1998 | Prutchi et al. | 607/22 |
| 5,899,928 | * 5/1999 | Sholder et al. | 607/27 |

OTHER PUBLICATIONS

Mussivand, T., et al., "A Transcutaneous Energy and Information Transfer System for Implanted Medical Devices", *ASAIO Journal*, 41 (3), M253–258, (Jul.–Sep. 1995).

* cited by examiner

*Primary Examiner*—Jeffrey R. Jastrzab
(74) *Attorney, Agent, or Firm*—Schwegman, Lundberg, Woessner & Kluth, P.A.

(57) ABSTRACT

A system is provided for optically communicating with an implantable device. In one embodiment, the system includes an implantable device having a large memory and an external unit which downloads information from the memory for analysis and display. The implantable device includes a light-emitting diode (LED) and a modulator for driving the LED. Although various frequencies can be used, frequencies which experience relatively little attenuation through body tissue are presently preferred. The external device includes a photo-multiplier tube (PMT) and a demodulator for equalizing and demodulating the detection signal produced by the PMT in response to detected light. A high bandwidth channel (perhaps as much as 500 Mbits/sec) is created by these components. This channel advantageously allows for a substantially reduced download time.

31 Claims, 4 Drawing Sheets

IMPLANTABLE DEVICE WITH OPTICAL TELEMETRY

BACKGROUND OF THE INVENTION

1. Field of the Invention

This invention relates generally to wireless communication systems for devices implanted in the body, and more particularly to optical communication between an implanted device and a device external to the body.

2. Description of the Related Art

Implantable devices have become a standard method of treating various medical conditions, many of which relate to the heart. Examples of devices which are routinely implanted include pacemakers, defibrillators, and nerve stimulators. These devices and others which have not yet become routine (such as implanted personal identification chips) are being provided with large memories for storing vast amounts of data. In the case of medical devices, this data may include physiological data such as the electrogram (electrical waveform at the electrodes), instantaneous heart rate, blood pressure, volume pumped, body temperature, etc., and configuration data such as mode of operation, amplifier sensitivity, filter bandwidth, and error messages. Often the device stores data that has been collected over a period of hours or days. This data is periodically retrieved by a doctor to monitor the patient's condition and to monitor the device's status. In response, the doctor might re-program the device for a different mode of operation, sensitivity setting, etc.

A method is needed to retrieve this data rapidly. The retrieval needs to be rapid so as to minimize the inconvenience to the patient who will usually have to remain in the doctor's office for the data retrieval process. To download four megabytes of medical device data, for example, at 20 Kbit/s would take nearly a half-hour—an undesirably long time for both the patient and medical professional or technician.

One method for data retrieval is the use of electromagnetic coupling between a pair of coils. One coil is excited to induce a current in the other. Modulation of the excitation signal can be detected in the induced current, and so communication is achieved. The problem with this is bandwidth. The coils each have a self-inductance which acts to attenuate high frequency signals, so that the bandwidth of communications is limited.

Another method for data retrieval is to provide a direct electrical connection. A wire connected to the implanted device is passed directly through the skin and coupled to the external device. Inherent with this technique is increased discomfort and increased risk of infection.

Thus, another method is needed to transfer a large amount of data quickly from the implanted device to the external device with minimal discomfort.

SUMMARY OF THE INVENTION

Accordingly, there is provided herein a system for communicating between an implantable device and an external device. In one embodiment, the system includes an implantable device having a large memory and an external unit which downloads information from the memory for analysis and display. The implantable device includes a light-emitting diode (LED) and a modulator for driving the LED. The LED emits a modulated light signal representing the data that is stored in memory. One light frequency range which may be used is $4.3 \times 10^{14} - 5.0 \times 10^{14}$ Hz, as body tissue exhibits good transmission in this range. The external device includes a photo-multiplier tube (PMT) for detecting and amplifying the modulated light signal, and a demodulator for equalizing and demodulating the detection signal produced by the PMT in response to modulated light.

These components will support a high bandwidth optical channel capable of carrying as much as 500 Mbit/s or more, and thereby provide for a substantially reduced data retrieval time. The implantable device may further include a receiver coil which has currents induced in response to a communication signal from the external device. A power converter may be coupled to the receiver coil to convert the induced currents into energy for powering the LED.

BRIEF DESCRIPTION OF THE DRAWINGS

Other objects and advantages of the invention will become apparent upon reading the following detailed description and upon reference to the accompanying drawings in which.

Figure 1:
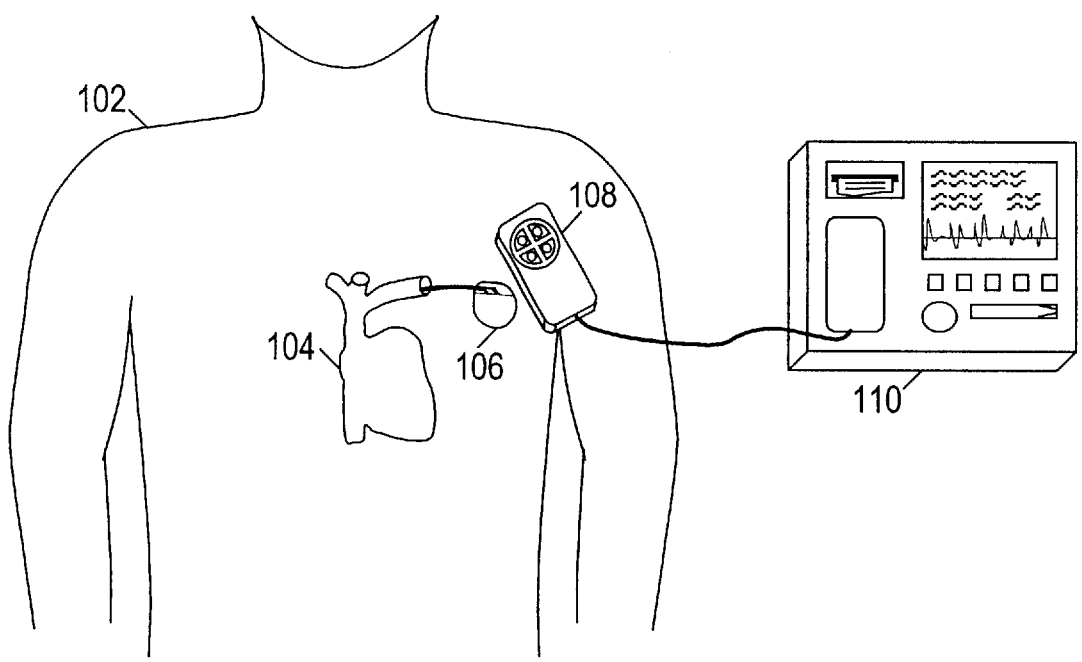
FIG. 1 shows an implantable medical device having optical telemetry, implanted in an environment within which a high-bandwidth channel would be desirably employed.

While the invention is susceptible to various modifications and alternative forms, specific embodiments thereof are shown by way of examples in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF PREFERRED EMBODIMENTS

The following description illustrates the principles of the invention with respect to an implantable pacemaker ("pacer") and an external device ("programmer"). The invention, however, is directed to an improved telemetry link between any implantable device and any external device configurable to download information from the implantable device. Thus, the invention applies to implantable cardioverter/defibrillators (ICD's), nerve stimulators, drug delivery devices, or any other implantable device configured to transmit data to an external device.

Turning now to the figures, FIG. 1 shows a human torso 102 having a heart 104 and an implanted pacer 106. Also shown is a wand 108 which is an extensible portion of an external programmer 110. Wand 108 is placed on an exterior surface of torso 102 near to the pacer 106. In the embodiment shown, pacer 106 is a pacemaker coupled to heart 104 to assist in regulating its operation. In any case, pacer 106 includes a memory for storing data for later retrieval. In the case of a pacemaker, the data may represent measured physiological signals such as cardiac voltages (EKG signals), blood temperatures, oxygen levels, sugar levels, etc.

Illustratively, programmer 110 is a programmer/analyzer for use by a physician. The programmer/analyzer operates to download information stored in pacer 106 by transmitting signals which place the pacer in a mode for downloading, and thereafter detecting signals sent by the device. Then, under control of the physician or other medical professional, the programmer/analyzer operates to analyze and display the information in a format which allows the physician to diagnose any problems. After performing an analysis, the physician may instruct the programmer/analyzer to adjust operating parameters of pacer 106. If this is the case, the programmer/analyzer provides new operating parameters to pacer 106.

Figure 2:
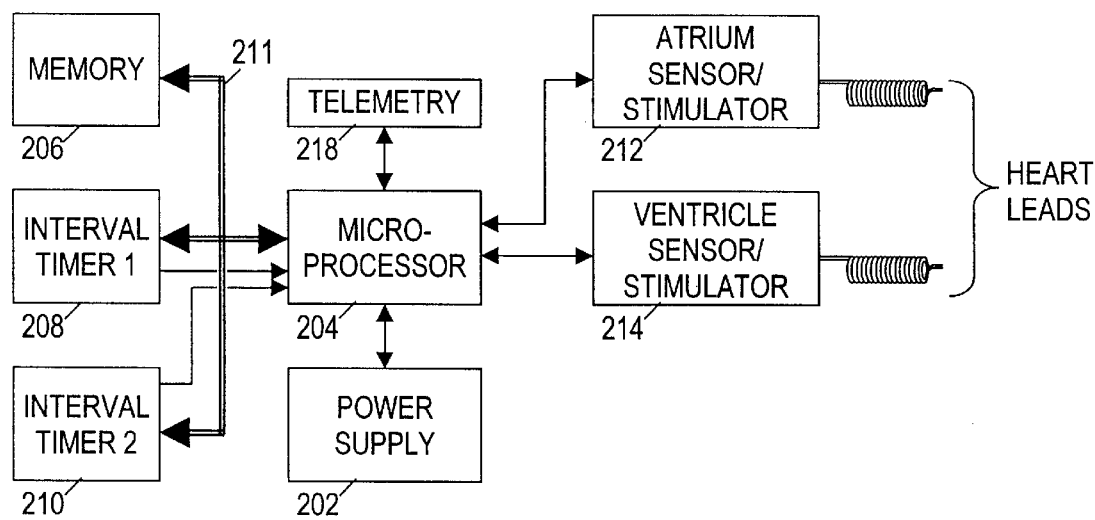
FIG. 2 is a block diagram of an implantable pacemaker/defibrillator.

FIG. 2 is a block diagram of an exemplary pacer 106. Pacer 106 has a power supply 202 coupled to a microprocessor 204. Power supply 202 provides support to all the devices shown in FIG. 2 through connections not shown. Microprocessor 204 is coupled to a memory 206, a first interval timer 208, and a second interval timer 210 via an I/O (input/output) bus 211. Microprocessor 204 is also coupled to control an atrium sensor/stimulator 212 and a ventricle sensor/stimulator 214, each of which may be coupled to the heart by flexible leads. Finally, microprocessor 204 is coupled to a telemetry module 218 to communicate with programmer 110.

Microprocessor 204 preferably is programmable and operates according to a program stored in a nonvolatile memory. The program often is parameterized—i.e. one or more of the operations the microprocessor performs is alterable by setting a parameter. For example, the microprocessor may be programmed to periodically trigger atrium stimulator 212. One of the parameters for this operation might be a value specifying the rate at which the stimulator is triggered. The parameters may be provided to microprocessor 204 via telemetry module 218 and stored in memory 206.

Pacer 106 in FIG. 2 uses first interval timer 208 to determine the delay between trigger signals applied to atrium stimulator 212 and ventricle stimulator 214. Further, second interval timer 210 measures the time since the last heartbeat sensed by the atrium sensor/stimulator 212 or ventricle sensor/stimulator 214. When either timer elapses, the elapsed timer asserts an interrupt to microprocessor 204 to notify microprocessor 204 that the set amount of time has passed. Microprocessor 204 determines the source of the interrupt and takes the appropriate action. For example, if a maximum time has elapsed since the last heartbeat, microprocessor 204 might trigger atrium sensor/stimulator 212.

Microprocessor 204 preferably also monitors one or more physiological signals. For example, microprocessor 204 may detect cardiac voltage signals via atrium sensor 212 and/or ventricle sensor 214. Blood pressure, body temperature, and adaptive configuration data may also be monitored. These signals preferably are logged in memory 206 for later retrieval by programmer 110. Memory 206 preferably is large enough to store a variety of physiological signals that are monitored over a period of several days. This amount of data may comprise several megabytes of data. Memory 206 preferably is implemented as dynamic random access memory (DRAM) or other suitable memory type.

Atrium sensor/stimulator 212 is an interface circuit between microprocessor 204 and a heart lead coupled to an atrium of the heart. Similarly, ventricle sensor/stimulator 214 is an interface circuit between microprocessor 204 and a heart lead that is coupled to a ventricle of the heart. These interface circuits are configured to apply a customized electrical energy pulse to the respective region of the heart in response to a trigger signal from microprocessor 204. Interface circuits 212, 214 may also be configured to measure cardiac voltage signals from the electrodes so that microprocessor 204 can monitor the performance of the heart. The microprocessor 204 may store the cardiac waveforms (or "electrograms") in memory for subsequent retrieval by a medical technician.

Telemetry module 218 may be designed to be activated by programmer 110 when wand 108 enters into proximity with pacer 106. This event causes telemetry module 218 to be activated and to notify microprocessor 204 of an incoming communication. Microprocessor 204 monitors the incoming communication from programmer 110 and stores programming data or parameters, and responds to any requests. For example, one request might be to transfer the data from memory 206 to programmer 110. In this case, microprocessor 204 provides the data from memory 206 to telemetry module 218 for transferal to programmer 110.

Figure 3:
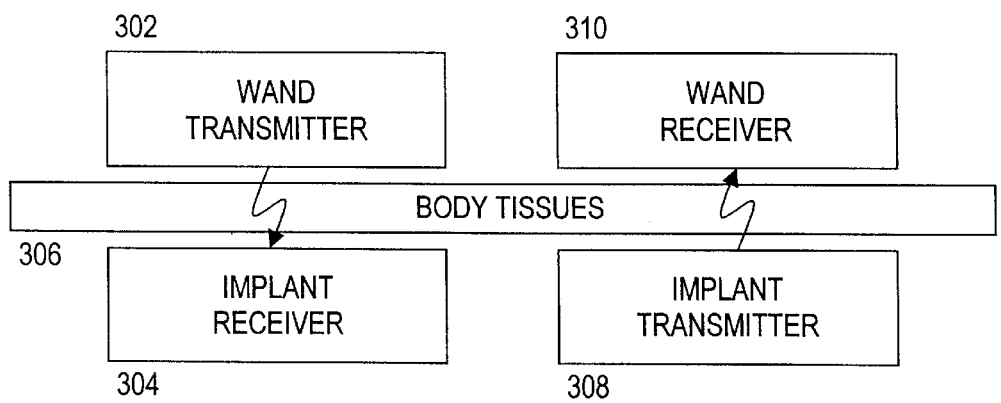
FIG. 3 is a schematic diagram illustrating communications between an implantable device and an external device.

FIG. 3 is a schematic diagram of the communications channels employed by pacer 106 and programmer 110. A wand transmitter 302 provides a communication signal which is transmitted to a pacer receiver 304 through body tissues 306. This communication signal, for example, might represent a programmer request for the pacer 106 to transmit data. This technique using a pair of coils is well known to those of ordinary skill in the art. An example of this technique is illustrated in U.S. Pat. No. 5,314,453, which is hereby incorporated by reference as though completely set forth herein.

To provide a download of a substantial amount of data in as short a time as possible from pacer 106 to programmer 110, a high bandwidth connection in the reverse direction (i.e. from the pacer to the programmer) is desired. This high-bandwidth connection comprises a pacer transmitter 308 which transmits a modulated light signal to a wand receiver 310 through body tissues 306. It is contemplated that wand transmitter 302 and implant receiver 304 are coils that communicate via a shared inductive coupling. Thus one embodiment uses an inductive coupling communications link for programmer 110 to transmit data and commands to pacer 106, and an optical communications link to transmit data and status information from pacer 106 to programmer 110. Alternatively, an optical link could be used to communicate in both directions.

It is contemplated that implant transmitter 308 includes an LED that emits light in the infrared (<$4.3 \times 10^{14}$ Hz), visible ($4.3 \times 10^{14}$–$7.3 \times 10^{14}$ Hz) or ultraviolet (>$7.3 \times 10^{14}$ Hz) frequency ranges, and that wand receiver 310 includes a light sensor sensitive to light emitted by implant transmitter 308. The various frequencies (colors) of light experience differing amounts of attenuation by body tissues 306. The light emitted by implant transmitter 308 preferably experiences relatively small losses while passing through body tissues 306. Experiments have been done using a light frequency of $5.42 \times 10^{14}$ Hz (green light), but somewhat lower frequencies such as $4.3 \times 10^{14}$–$5.0 \times 10^{14}$ Hz may be preferred, and $4.5 \times 10^{14}$–$4.7 \times 10^{14}$ Hz may be more preferred.

Figure 4:
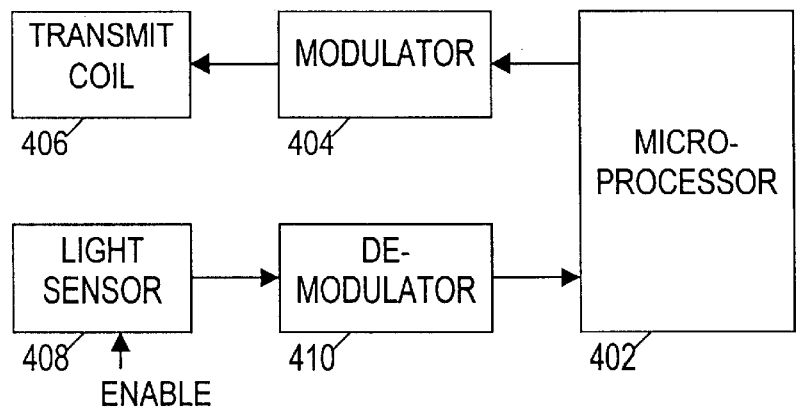
FIG. 4 is a block diagram of portions of an external device.

FIG. 4 is a block diagram of portions of one embodiment of a programmer 110. Programmer 110 includes a microprocessor 402, a modulator 404, a transmit coil 406, a light sensor 408, and a demodulator 410. Microprocessor 402 accepts and responds to user input (via controls not shown) and initiates communications with pacer 106. For example, if a user requests a download of data from pacer 106 to programmer 110, microprocessor 402 formulates a command signal, and sends the signal to modulator 404. Modulator 404 converts the command signal into a modulated signal for driving transmit coil 406. The signal driving the transmit coil produces a changing magnetic field which induces a current in a receive coil in pacer 106. Pacer 106 processes the induced current in a manner described further below. Pacer 106 can transmit signals to programmer 110 by modulating a light signal. The modulated light signal may be greatly attenuated by body tissues. When enabled, light sensor 408 detects and amplifies the modulated light signal to produce a detection signal. Demodulator 410 demodulates the detection signal and converts it into the data transmitted by the pacer 106. Demodulator 410 then provides the data to microprocessor 402 for eventual analysis and display.

Because the optical signal may be greatly attenuated (i.e. reduced in intensity) by body tissue, light sensor 408 preferably is highly sensitive and must be protected from ambient light. This protection may be provided in the form of an enable signal which is asserted only when the ambient light is blocked, e.g. when the wand is pressed flat against the torso. In one implementation, the enable signal may be asserted when a mechanical switch is closed upon pressing the wand against the torso. In another implementation, the enable signal may be asserted when a photo-transistor adjacent to the light sensor 408 detects that the light intensity has fallen below a predetermined threshold.

One light sensor which is contemplated for use in wand 108 is a PMT (photo-multiplier tube) such as R5600-01 PMT from Hamamatsu Corporation. PMT's are well known and widely available, and are able to detect single photons while maintaining a low noise level. This light sensor is advantageously sensitive to light in the frequency range from $4.3 \times 10^{14}$ to $20.0 \times 10^{14}$ Hz.

In another embodiment, light sensor 408 comprises a photo-diode which may be robust enough to withstand ambient light and sensitive enough to detect attenuated light emissions from the pacer. This light sensor advantageously does not require an enable signal and the means for generating the enable signal.

Figure 5:
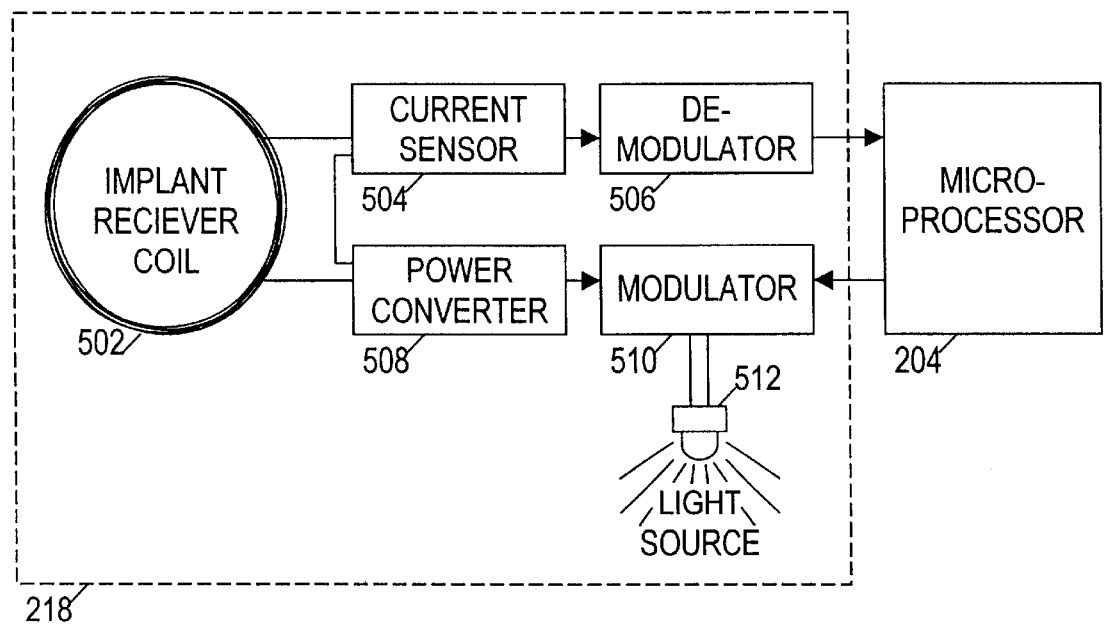
FIG. 5 is a block diagram of a telemetry module which supports an optical communications link.

FIG. 5 shows a block diagram of an illustrative telemetry module 218 of pacer 106. Telemetry module 218 comprises an implant receiver coil 502, a current sensor 504, a demodulator 506, a power converter 508, a modulator 510, and a light source 512. A communication signal from wand 108 induces a current in coil 502. Current sensor 504 detects the induced currents and produces an amplified detection signal representative of the communication signal sent by wand 108. Demodulator 506 demodulates the communication signal to obtain the commands, data and/or parameters being sent by wand 108. Microprocessor 204 processes the demodulated signal and determines an appropriate response. For example, if the transmitted data represents a download request, microprocessor 204 will initiate a download of the requested data stored in memory 206, i.e. the microprocessor will cause data from memory 206 to be supplied to modulator 510.

Referring still to FIG. 5, power converter 508 is coupled to implant receiver coil 502 to convert the induced currents into stored energy. As modulator 510 converts the data from microprocessor 204 into a modulated signal, it uses stored energy from power converter 508 to drive light source 512 in accordance with the modulated signal. Light source 512 may be an LED (light emitting diode) which emits light with a frequency suitable to pass through the body to the wand. Preferably the LED emits light with a frequency between $4.3 \times 10^{14}$ and $5.0 \times 10^{14}$ Hz, but other frequencies may be used as well. The light emitted is modulated in accordance with the modulated signal from modulator 510. The modulated light may be detected and demodulated by wand 108 to recover the data stored in memory 206 as described above.

In one embodiment, power converter 508 employs a full-wave rectifier to convert the currents induced in coil 502 into a unidirectional charging current. The power converter also includes a bank of switching capacitors to be charged by the unidirectional charging current and thereafter step up the voltage to charge an energy storage capacitor. Current sensor 504 may be configured to detect the induced currents by sensing the voltage drop across one or more diodes in the full-wave rectifier.

In another embodiment, the LED is powered by power supply 202 of pacer 106. Power converter 508 may be included for the purpose of recharging power supply 202.

Various modulation schemes may be employed for the communication channels. The wand-to-implant communications channel may use pulse-width modulation (PWM), frequency-shift keying (FSK), or other suitable techniques. The implant-to-wand communications channel may also employ any suitable techniques such as pulse-code modulation (PCM) and simplex signaling. Both channels may employ channel coding for error detection, timing, and/or constraining power usage. Such channel coding techniques are known to those of ordinary skill in the art. It is noted that light sensor 408 may be configured to generate a detection signal which is proportional to the light intensity, and that consequently both digital and analog amplitude modulation signaling is also supported by the contemplated configuration.

Figure 6:
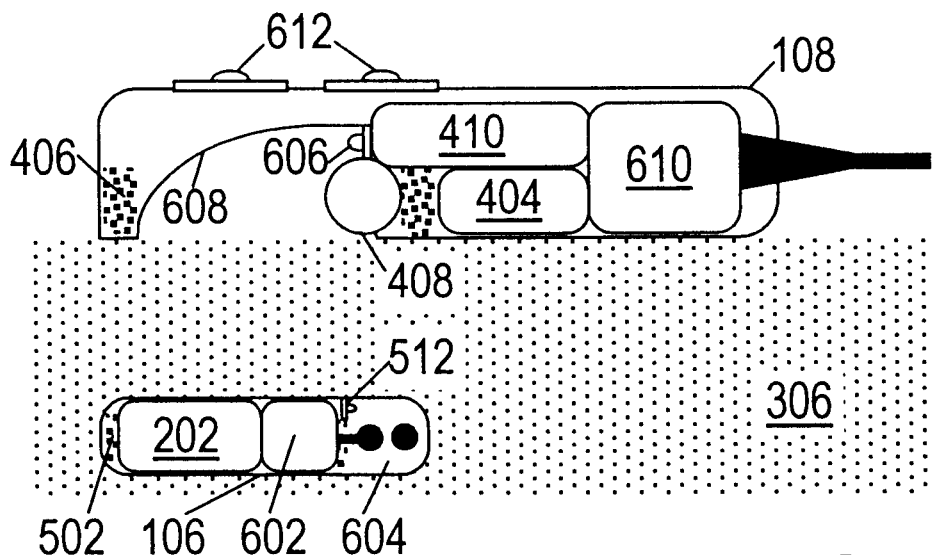
FIG. 6 shows an exemplary configuration of the system.

FIG. 6 shows an exemplary configuration of wand 108 and pacer 106 shown in cross-section. Wand 108 is pressed against body tissues 306 proximate to the location of pacer 106 and in active communication with pacer 106. Pacer 106 comprises power supply 202, electronics module 602, implant receiver coil 502, light source 512, and header 604. Electronics module 602 includes microprocessor 204, memory 206, timers 208, 210, sensor/stimulators 212, 214, current sensor 504, demodulator 506, power converter 508, and modulator 510. Electronics module 602 and the components it contains may be constructed as a circuit board. Header 604 is a transparent portion of pacer 106 which may include electrical connectors for the heart leads (FIG. 2) and light source 512. Alternatively, light source 512 may be located in electronics module 602. As electronics module 602 is normally placed in an opaque portion of pacer 106, light source 512 is configured to emit light in the direction of the transparent header 604. A mirror may be located within header 604 to redirect the modulated light toward wand 108. This mirror may be concave to reduce dispersion of the modulated light signal. For either placement of light source 512, header 604 may also have a portion of its exterior surface configured as a lens to reduce the dispersion of the modulated light signal. Some of these configurations are described in U.S. Pat. No. 5,556,421, which is hereby incorporated by reference in its entirety.

Wand 108 illustratively comprises modulator 404, transmit coil 406, light sensor 408, demodulator 410, ambient light detector 606, reflective surface 608, interface module 610, and user interface 612. In one embodiment, light sensor 408 is placed near a convergence point of light rays that reflect from reflective surface 608. Reflective surface 608 is designed to increase the light-gathering ability of wand 108. Ambient light detector 606 is positioned within the concavity defined by reflective surface 608 and/or adjacent to light sensor 408. Ambient light detector 606 provides the enable signal discussed in FIG. 4 when a sensitive light sensor 408 is employed. Ambient light detector 606 may be a photo-transistor or photo-diode or any other photo-sensitive device robust enough to withstand anticipated light levels when wand 108 is separated from torso 102. Interface module 610 may be a line driver/buffer for communications with the rest of programmer 110, and may further comprise a power supply or converter for powering the electronics of wand 108. User interface 612 may comprise buttons for user input (e.g. begin download) and lights for user feedback regarding the status of the communications link with the implanted device. Directional lights may also be provided to aid the user in positioning the wand to achieve the highest communications signal-to-noise ratio and the maximum communications rate for downloading information from the memory of the pacer.

Figure 7:
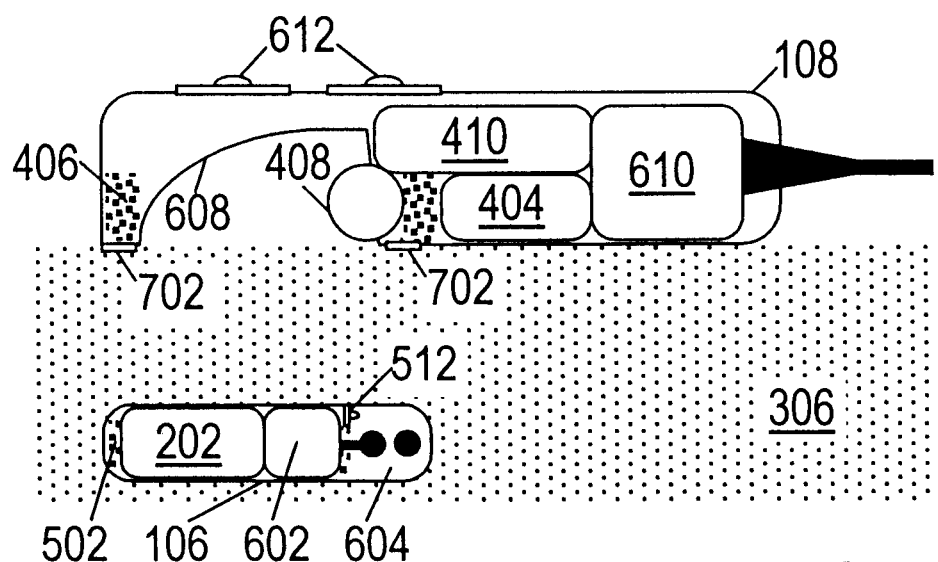
FIG. 7 shows a second exemplary configuration of the system.

FIG. 7 shows a second exemplary configuration of wand 108, in which mechanical switches 702 rather than ambient light detector 606 are used to provide the enable signal of FIG. 4. Mechanical switches 702 are pressure sensitive and positioned on the face of the wand so that when the wand is correctly pressed against the torso, the normally open switches are all closed. Variations on this may be employed so long as the enable signal is only asserted when the light sensor 408 is shielded from excessive light levels.

Numerous variations and modifications will become apparent to those skilled in the art once the above disclosure is fully appreciated. It is intended that the following claims be interpreted to embrace all such variations and modifications.

What is a claimed is:

1. An implantable device capable of supporting a high-bandwidth optical communications link with an external device, wherein the implantable device comprises:
 a memory configured to store data for later retrieval;
 a photo-emitter configured to generate light having a transmission frequency;
 a modulator coupled to receive data from the memory and configured to convert the data into an electrical signal for driving the photo-emitter;
 a receiver coil configured to generate an induced current in response to a communication signal from the external device;
 a current sensor configured to detect the induced current in the receiver coil and to convert the induced current into a detected signal;
 a demodulator coupled to the current sensor to receive the detected signal and configured to convert the detected signal into an operational signal for the implantable device; and
 a microprocessor coupled to the demodulator and the memory, wherein the microprocessor receives the operational signal from the demodulator, collects the data for transmission to the external device, and stores the collected data in the memory.

2. The implantable device of claim 1, wherein the transmission frequency is in a frequency range from approximately $4.3 \times 10^{14}$ to approximately $20.0 \times 10^{14}$ Hz.

3. The implantable device of claim 1, wherein the transmission frequency is in a frequency range from approximately $4.3 \times 10^{14}$ to approximately $7.3 \times 10^{14}$ Hz.

4. The implantable device of claim 1, wherein the transmission frequency is in a frequency range from approximately $4.5 \times 10^{14}$ to approximately $4.7 \times 101^{14}$ Hz.

5. The implantable device of claim 1, wherein the microprocessor is coupled to a stimulus generator which operates in response to a trigger signal provided by the microprocessor, and wherein the operational signal is used to determine trigger signal characteristics.

6. The implantable device of claim 1, further comprising a power converter coupled to the receiver coil and configured to convert the induced current into power to be supplied to the modulator.

7. The implantable device of claim 1, further comprising a power converter coupled to the receiver coil and the modulator to convert induced current from the receiver coil into electrical power to operate the photo-emitter.

8. The implantable device of claim 1, further comprising a sensor configured to sample heart-generated electrical signals and coupled to the microprocessor to provide the sampled signals for storage in the memory.

9. A system for transcutaneous communication, wherein the system comprises:
 an implantable device which includes:
  a memory configured to store data for later retrieval;
  a photo-emitter configured to generate light in response to a modulated signal, wherein the photo-emitter generates light in a frequency range;
  an implantable device modulator coupled to receive data from the memory and configured to convert the data into the modulated signal for driving the photo-emitter;
  a receiver coil configured to generate an induced current in response to a changing magnetic field, wherein the induced current is representative of a communication signal;
  a current sensor configured to detect the induced current in the receiver coil and to convert the induced current into an internal detected signal;
  an implantable device demodulator coupled to receive the internal detected signal from the current sensor and configured to convert the internal detected signal into an operational signal for the implantable device;
 an external unit which includes:
  a photo-multiplier configured to detect light emitted by the photo-emitter and configured to responsively generate an external detection signal;
  an external unit demodulator coupled to the photo-multiplier to receive the external detection signal and configured to convert the external detection signal into a data signal;
  a display coupled to the external unit demodulator to receive the data signal and configured to produce an output display representative of the data signal;
  an external unit microprocessor configured to generate the communication signal;
  an external unit modulator coupled to receive the communication signal from the external unit microprocessor and configured to generate a modulated communication signal; and
  a transmitter coil coupled to the external unit modulator and driven by the modulated communication signal, the transmitter coil configured to produce the changing magnetic field.

10. The system of claim 9, wherein the light produced by the photo-emitter has a frequency in a range from approximately $4.3 \times 10^{14}$ to approximately $20.0 \times 10^{14}$ Hz.

11. The system of claim 9, wherein the operational signal for the implantable device is selected from the group consisting of a command signal, a data signal and a parameter signal.

12. The system of claim 9, wherein the implantable device further includes a sensor configured to sample heart-generated electrical signals and coupled to the memory to provide the sampled signals for storage in the memory.

13. The system of claim 9, wherein the implantable device further includes:
   a power converter coupled to the receiver coil to convert the induced current into energy; and
   a capacitor coupled to the power converter to receive and store the energy, and configured to supply the energy to the implantable device modulator for conversion into the modulated signal.

14. A method for transcutaneous communication to an external device, wherein the method comprises:
   retrieving stored data from a memory in an implanted device;
   converting the stored data into a modulation signal;
   applying the modulation signal to a photo-emitter to produce light;
   positioning a photo-multiplier tube to detect the light;
   converting the light into a detection signal;
   demodulating the detection signal to reproduce the stored data;
   generating a programming signal in the external device;
   driving a signaling coil with the programming signal;
   inducing a current in a receiving coil in the implanted device;
   converting the induced current into stored energy on a capacitor; and
   using the stored energy to produce the modulation signal.

15. The method of claim 14, wherein the light produced by the photo-emitter has a frequency in a range from approximately $4.3 \times 10^{14}$ to approximately $20.0 \times 10^{14}$ Hz.

16. The method of claim 14, further comprising:
   demodulating the induced current into program data; and
   storing the program data in the memory in the implanted device.

17. A system to provide optical communications, comprising:
   an implantable device that includes:
      a memory that stores information;
      a light-emitting diode (LED) that emits the information;
      a modulator to drive the LED so as to emit a modulated light signal;
      a receiver coil that induces currents in response to a changing magnetic field; and
      a power converter coupled to the receiver coil to convert the currents into energy for powering the LED;
   an external device that includes:
      a photo-multiplier tube to detect the modulated light signal;
      a demodulator to demodulate the modulated light signal to obtain the information, wherein the LED, the modulator, the photo-multiplier tube, and the demodulator are adapted to support optical communications; and
      a transmitter coil configured to produce the changing magnetic field.

18. The system of claim 17, wherein the frequency of the optical communications is in a range from approximately $4.3 \times 10^{14}$ to approximately $20.0 \times 10^{14}$ Hz.

19. The system of claim 17, wherein the external device further includes a microprocessor to generate a communication signal and an external device modulator to convert the communication signal into a modulated communication signal, and wherein the transmitter coil is driven by the modulated communication signal to produce the changing magnetic field, and wherein the implantable device further includes a current sensor to detect the induced current in the receiver coil and to convert the induced current into a detected signal, and an implantable device demodulator to convert the detected signal into an operational signal for the implantable device.

20. A system to provide communications, comprising:
   an implantable device that includes:
      an implantable transmitter that transmits information;
      an implantable receiver that receives commands;
   an external device that includes:
      an external transmitter that transmits the commands; and
      an external receiver that receives the information, wherein the implantable receiver receives and the external transmitter transmits via an inductive link, and the implantable transmitter transmits and the external receiver receives via an optical link.

21. The system of claim 20, wherein the implantable transmitter includes a light-emitting diode that emits light with a frequency in a range from approximately $4.3 \times 10^{14}$ to $20.0 \times 10^{14}$ Hz.

22. A programmer that supports high bandwidth communications, comprising:
   a microprocessor that presents a command;
   a modulator that converts the command to a modulated signal;
   a transmit coil that changes a magnetic field in response to the modulated signal;
   a demodulator that demodulates a detection signal to form information; and
   a light sensor that presents the detection signal to the demodulator, wherein the light sensor includes an enabling signal to enable detection of a modulated light signal to produce the detection signal.

23. The programmer of claim 22, wherein the enabling signal issues so as to enable detection of the modulated light signal when a mechanical switch indicates the absence of ambient light at the light sensor.

24. The programmer of claims 22, wherein the enabling signal issues so as to enable detection of the modulated light signal when a photo-sensitive device senses that ambient light at the light sensor is below a predetermined threshold.

25. The programmer of claim 22, wherein the light sensor includes a photo-multiplier tube.

26. The programmer of claim 24, wherein the photo-sensitive device is located adjacent to the light sensor.

27. A telemetry module in an implantable device, comprising:
   an implant receiver coil that produces a current responsive to a modulated signal;
   a current sensor that senses the current and produces the modulated signal;
   a demodulator that demodulates the modulated signal to produce a signal;
   a microprocessor receptive to the signal to produce a response;
   a power converter that converts the current into energy and stores the energy;
   a modulator to modulate the response to form a modulated response; and a light source to emit light with a frequency so as to transmit the modulated response to a desired destination.

28. The telemetry module of claim 27, wherein the light source uses the energy that is stored by the power converter to emit light.

29. The telemetry module of claim 27, wherein the power converter includes a full-wave rectifier to convert the current into a unidirectional charging current.

30. The telemetry module of claim 29, wherein the power converter further includes a number of switching capacitors to be charged by the unidirectional charging current so as to charge an energy storage capacitor.

31. The telemetry module of claim 30, wherein the demodulator is adapted to use a demodulation technique selected from a group consisting of pulse-width demodulation and frequency-shift keying, and wherein the modulator is adapted to use a modulation technique selected from a group consisting of pulse-code modulation and simplex signaling.

* * * * *

UNITED STATES PATENT AND TRADEMARK OFFICE
CERTIFICATE OF CORRECTION

PATENT NO. : 6,243,608 B1  Page 1 of 1
DATED : June 5, 2001
INVENTOR(S) : Pauly et al.

It is certified that error appears in the above-identified patent and that said Letters Patent is hereby corrected as shown below:

Column 8, claim 4,
Line 3, delete "4.7 x $101^{14}$ Hz" and insert -- 4.7 x $10^{14}$ Hz --, therefor.

Column 10, claim 24,
Line 45, delete "claims" and insert -- claim --, therefor.

Signed and Sealed this

Eighteenth Day of December, 2001

*Attest:*

JAMES E. ROGAN
*Attesting Officer*  *Director of the United States Patent and Trademark Office*